(12) United States Patent
Lin et al.

(10) Patent No.: US 9,090,663 B2
(45) Date of Patent: Jul. 28, 2015

(54) SYSTEMS AND METHODS FOR THE CAPTURE AND SEPARATION OF MICROPARTICLES

(75) Inventors: Qiao Lin, New York, NY (US); Yao Zhou, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 482 days.

(21) Appl. No.: 12/764,898

(22) Filed: Apr. 21, 2010

(65) Prior Publication Data

US 2010/0297733 A1 Nov. 25, 2010

Related U.S. Application Data

(60) Provisional application No. 61/171,331, filed on Apr. 21, 2009.

(51) Int. Cl.
| | |
|---|---|
| *C12M 1/00* | (2006.01) |
| *C07K 1/14* | (2006.01) |
| *C12Q 1/68* | (2006.01) |
| *G01N 35/00* | (2006.01) |
| *C12M 1/42* | (2006.01) |

(Continued)

(52) U.S. Cl.
CPC . *C07K 1/14* (2013.01); *B03C 1/288* (2013.01); *C12M 35/00* (2013.01); *C12Q 1/6883* (2013.01); *G01N 35/0098* (2013.01); *B01D 21/0009* (2013.01); *B03C 2201/26* (2013.01)

(58) Field of Classification Search
None
See application file for complete search history.

(56) References Cited

U.S. PATENT DOCUMENTS

| | | | |
|---|---|---|---|
| 5,508,164 A | 4/1996 | Kausch et al. | |
| 5,968,820 A | 10/1999 | Zborowski et al. | |
| 5,998,588 A | 12/1999 | Hoffman et al. | |

(Continued)

FOREIGN PATENT DOCUMENTS

| | | |
|---|---|---|
| EP | 1 903 338 | 3/2008 |
| KR | 1020090032457 | 5/2009 |

(Continued)

OTHER PUBLICATIONS

Suzuki et al "Chaotic mixing of magnetic beads in microcell separator" Proc. 3rd INt. Symp. Turbulence and Shear Flow Phenomena, Jun. 24-27, 2003, pp. 817-822.*

(Continued)

*Primary Examiner* — Betty Forman
(74) *Attorney, Agent, or Firm* — Baker Botts, LLP

(57) ABSTRACT

Systems and methods are provided for capturing and/or isolating target microparticles. In one aspect, a method for capturing target microparticles is disclosed. The method includes: forming a fluid including the target microparticles, non-target microparticles, and magnetic beads, the magnetic beads having a stronger affinity with the target microparticles than with the non-target microparticles; flowing the fluid through a multidirectional microchannel; and applying a magnetic field to the fluid while the fluid is flowing through at least a portion of the microchannel to effect capture of at least a portion of the target microparticles onto the magnetic beads. Such a method can further includes passing the fluid having exited from the microchannel through a separator while subjecting the fluid to a second magnetic field so as to isolate the target microparticles. In addition, devices and systems are disclosed for capturing and/or isolating target microparticles based on magnetic manipulation.

8 Claims, 11 Drawing Sheets

(51) Int. Cl.
B03C 1/28 (2006.01)
B01D 21/00 (2006.01)

(56) References Cited

U.S. PATENT DOCUMENTS

| | | | |
|---|---|---|---|
| 6,344,326 B1* | 2/2002 | Nelson et al. | 435/6.12 |
| 6,479,242 B1 | 11/2002 | Guo et al. | |
| 6,641,783 B1 | 11/2003 | Pidgeon et al. | |
| 6,887,693 B2 | 5/2005 | McMillan et al. | |
| 7,029,852 B2 | 4/2006 | Liebholz et al. | |
| 7,141,375 B2 | 11/2006 | Pietras et al. | |
| 7,151,167 B2 | 12/2006 | Gjerde et al. | |
| 7,217,542 B2 | 5/2007 | Tyvoll et al. | |
| 7,285,412 B2* | 10/2007 | Casagrande et al. | 435/297.1 |
| 7,338,762 B2 | 3/2008 | Gorenstein et al. | |
| 7,413,712 B2 | 8/2008 | Liu et al. | |
| 7,887,753 B2 | 2/2011 | Quake et al. | |
| 7,932,034 B2 | 4/2011 | Esfandyarpour et al. | |
| 7,964,356 B2 | 6/2011 | Zichi et al. | |
| 8,124,015 B2 | 2/2012 | Diercks et al. | |
| 2004/0005582 A1 | 1/2004 | Shipwash | |
| 2004/0043509 A1* | 3/2004 | Stahler et al. | 436/518 |
| 2004/0126890 A1 | 7/2004 | Gjerde et al. | |
| 2004/0241718 A1 | 12/2004 | McGown | |
| 2005/0069910 A1 | 3/2005 | Turner et al. | |
| 2005/0142582 A1 | 6/2005 | Doyle et al. | |
| 2005/0208487 A1 | 9/2005 | Burmeister et al. | |
| 2005/0250117 A1 | 11/2005 | Su et al. | |
| 2006/0172429 A1 | 8/2006 | Nilsson et al. | |
| 2006/0205061 A1 | 9/2006 | Roukes | |
| 2007/0122811 A1 | 5/2007 | Buzby | |
| 2007/0184456 A1 | 8/2007 | Chee et al. | |
| 2007/0292397 A1 | 12/2007 | McNulty et al. | |
| 2008/0014576 A1* | 1/2008 | Jovanovich et al. | 435/5 |
| 2008/0056946 A1 | 3/2008 | Ahmad | |
| 2008/0132188 A1 | 6/2008 | Nivio et al. | |
| 2008/0245971 A1 | 10/2008 | Wimberger-Friedl et al. | |
| 2008/0264842 A1 | 10/2008 | Hukari et al. | |
| 2009/0011451 A1 | 1/2009 | Rodriguez et al. | |
| 2009/0048124 A1 | 2/2009 | Leamon et al. | |
| 2009/0166196 A1 | 7/2009 | Kayyem | |
| 2009/0227044 A1* | 9/2009 | Dosev et al. | 436/526 |
| 2010/0151465 A1 | 6/2010 | Ju et al. | |
| 2010/0279283 A1 | 11/2010 | Raghunath et al. | |
| 2011/0143949 A1 | 6/2011 | Heid et al. | |
| 2012/0028811 A1 | 2/2012 | Craighead et al. | |
| 2014/0038301 A1 | 2/2014 | Ju et al. | |
| 2014/0248621 A1 | 9/2014 | Collins | |

FOREIGN PATENT DOCUMENTS

| | | |
|---|---|---|
| WO | WO 2005/021725 | 3/2005 |
| WO | WO 2007/092713 | 8/2007 |
| WO | WO 2008/042481 | 4/2008 |
| WO | WO 2009/140326 | 11/2009 |
| WO | WO 2010/123521 | 10/2010 |
| WO | WO 2013/044240 | 3/2013 |

OTHER PUBLICATIONS

Inokuchi et al "development of micro immuno-magnetic cell sorting system with lamination mixer and magnetic separator" Proc. 25th Sensor Symp. 2008, pp. 1-2.*
Nguyen, T. et al., 2009, An aptamer-based microfluidic device for thermally controlled affinity extraction, Microfluidics and Nanofluidics, 6(4): 479-487.
Written Opinion of the International Searching Authority for PCT/US2008/057433: International Filing Date: Mar. 27, 2008.
U.S. Appl. No. 12/568,651, filed Sep. 28, 2009.
U.S. Appl. No. 12/568,651, filed Mar. 12, 2012 Response to Non-Final Office Action.
K.Y. Lien, J. L. Lin, C. Y. Liu, H. Y. Lei, and G. B. Lee, "Purification and Enrichment of Virus Samples Utilizing Magnetic Beads on a Microfluidic System," Lab on a Chip, vol. 7, pp. 868-875, 2007.
V. I. Furdui and D. J. Harrison, "Immunomagnetic T Cell Capture from Blood for Pcr Analysis Using Microfluidic Systems," Lab on a Chip, vol. 4, pp. 614-618, 2004.
C. M. Earhart, R. J. Wilson, R. L. White, N. Pourmand, and S. X. Wang, "Microfabricated Magnetic Sifter for High-Throughput and High-Gradient Magnetic Separation," Journal of Magnetism and Magnetic Materials, vol. 321, pp. 1436-1439, 2009.
M. Berger, J. Castelino, R. Huang, M. Shah, and R. H. Austin, "Design of a Microfabricated Magnetic Cell Separator," Electrophoresis, vol. 22, pp. 3883-3892, 2001.
D. W. Inglis, R. Riehn, R. H. Austin, and J. C. Sturm, "Continuous Microfluidic Immunomagnetic Cell Separation," Applied Physics Letters, vol. 85, pp. 5093-5095, 2004.
J. D. Adams, U. Kim, and H. T. Soh, "Multitarget Magnetic Activated Cell Sorter," Proceedings of the National Academy of Sciences of the United States of America, vol. 105, pp. 18165-18170, 2008.
M. A. Espy, H. Sandin, C. Carr, C. J. Hanson, M. D. Ward, and R. H. Kraus, "An Instrument for Sorting of Magnetic Microparticles in a Magnetic Field Gradient," Cytometry Part A, vol. 69A, pp. 1132-1142, 2006.
C. C. Chang and R. J. Yang, "Electrokinetic Mixing in Microfluidic Systems," Microfluidics and Nanofluidics, vol. 3, pp. 501-525, 2007.
V. Hessel, H. Lowe, and F. Schonfeld, "Micromixers—a Review on Passive and Active Mixing Principles," pp. 2479-2501, 2005.
R. H. Liu, M. A. Stremler, K. V. Sharp, M. G. Olsen, J. G. Santiago, R. J. Adrian, H. Aref, and D. J. Beebe, "Passive Mixing in a Three-Dimensional Serpentine Microchannel," Journal of Microelectromechanical Systems, vol. 9, pp. 190-197, 2000.
N. T. Nguyen and Z. G. Wu, "Micromixers—a Review," Journal of Micromechanics and Microengineering, vol. 15, pp. R1-R16, 2005.
M. D. Estes, J. Do, and C. H. Ahn, "On Chip Cell Separator Using Magnetic Bead-Based Enrichment and Depletion of Various Surface Markers," Biomedical Microdevices, vol. 11, pp. 509-515, 2009.
T. Lund-Olesen, M. Dufva, and M. F. Hansen, "Capture of DNA in Microfluidic Channel Using Magnetic Beads: Increasing Capture Efficiency with Integrated Microfluidic Mixer," pp. 396-400, 2007.
A. D. Stroock, S. K. W. Dertinger, A. Ajdari, I. Mezic, H. A. Stone, and G. M. Whitesides, "Chaotic Mixer for Microchannels," Science, vol. 295, pp. 647-651, 2002.
E. Verpoorte, "Beads and Chips: New Recipes for Analysis," Lab on a Chip, vol. 3, pp. 60N-68N, 2003.
Y. Xu, J.A. Phillips, J. Yan, Q. Li, Z. H. Fan, and W. Tan, "Aptamer-Based Microfluidic Device for Enrichment, Sorting, and Detection of Multiple Cancer Cells," Anal. Chem., vol. 81, pp. 7436-7442, 2009.
N. Pamme and C. Wilhelm, "Continuous Sorting of Magnetic Cells via On-Chip Free-Flow Magnetophoresis," Lab on a Chip, vol. 6, pp. 974-980, 2006.
S.-H. Oh, A.K. Singh, P.H. Bessette, S.A. Kenrick, J.J. Rice, J. Qian, P.S. Daugherty, and H.T. Soh. "Screening of Molecular Libraries Using the Continuous-Flow, Micro-Magnetic Cell Sorter," 10th Intl Conf. on Miniaturized Systems for Chemistry and Life Sciences, Nov. 5-9, 2006, Tokyo, Japan, pp. 975-977.
AAAT Bioquest, "Classic reactive flourescent labeling dyes & their applications", *AAT Bioquest, Inc. Product Technical Information Sheet*, 2010 [online]. Retrieved on Jan. 29, 2013 at http://www.biomol.de.details/AB/Classic_Reactive_Flourescent_Labeling_Dyes.pdf>.
Blazej, et al., "Microfabricated bioprocessor for integrated nanoliter-scale Sanger DNA sequencing", *PNAS*, 103(19):7240-7245 (2006).
U.S. Appl. No. 13/652,214, filed Oct. 15, 2012.
Bock, et al., "Selection of single-stranded-DNA molecules that bind and inhibit human thrombin", *Nature*, 355:564-566 (1992).
Brody, et al., "The use if aptamers in large arrays for molecular diagnostics", *Molecular Diagnosis*, 4(4):381-388 (1999).
Broyles, et al., "Sample filtration, concentration, and separation integrated on microfluidic devices", *Anal. Chemistry*, 75:2761-2767 (2003).
Burgstaller, et al., "Aptamers as tools for target prioritization and lead identification" *Drug Discovery Today*, 7(24):1221-1228 (2002).
Chen, et al., "Total nucleic acid analysis integrated on microfluidic devices", *Lab on a Chip*, 7(11):1413-1423 (2007).

(56) References Cited

OTHER PUBLICATIONS

Cho, et al., "PDMS-glass serpentine microchannel chip for time domain PCR with bubble suppression in sample injection", *Journal of Micromechanics and Microengineering*, 17(9):1810-1817 (2007).
Chou, et al., "A microfabricated device for sizing and sorting DNA molecules", *PNAS*, 96(1):11-13 (1999).
Collett, et al., "Functional RNA microarrays for high-throughput screening of antiprotein aptamers", *Analytical Biochemistry*, 338(1):113-123 (2005).
Cox, et al., "Automated selection of anti-protein aptamers", *Bioorganic & Medicinal Chemistry*, 9(10):2525-2531 (2001).
Dahlin, et al., "Poly(dimethylsiloxane)-based microchip for two-dimensional solid-phase extraction-capillary electrophoresis with an integrated electrospray emitter tip", *Analytical Chemistry*, 77(16):5356-5363 (2005).
Darby, R., *Chemical Engineering Fluid Mechanics*, 2nd Edition, Revised and Expanded, (Marcel Dekker, New York, 2001) (Table of Contents).
Deng, et al., "Aptamer affinity chromatography for rapid assay of adenosine in microdialysis samples collected in vivo", *Journal of Chromatography A*, 1005(1-2):123-130 (2003).
Diehl, et al., "BEAMing: single-molecule PCR on microparticles in water-in-oil emulsions", *Nature Methods*, 3(7):551-559 (2006).
Dittmer, et al., "A DNA-based machine that can cyclically bind and release thrombin", *Angewandte Chemie-International Edition*, 43(27):3550-3553 (2004).
Doherty, et al., "Sparsely cross-linked "nanogel" matrixes as fluid, mechanically stabilized polymer networks for high-throughput microchannel DNA sequencing", *Anal. Chem.*, 76:5249-5256 (2004).
D'Orazio, et al., "Biosensors in clinical chemistry" *Clinica Chimica Acta*, 334:41-69 (2003).
Drabovich, et al., "Selection of smart aptamers by equilibrium capillary electrophoresis of equilibrium mixtures (ECEEM)", *Journal of the American Chemical Society*, 127(32):1 1224-11225 (2005).
Drabovich, et al., "Selection of smart aptamers by methods of kinetic capillary electrophoresis", *Anal. Chem.*, 78(9)3171-3178 (2006).
El-Ali, et al., "Cell stimulus and lysis in a microfluidic device with segmented gas-liquid flow", *Analytical Chemistry*, 77(11):3629-3636 (2005).
Farokhzad, et al., "Targeted nanoparticle-aptamer bioconjugates for cancer chemotherapy in vivo", *PNAS*, 103(16):6315-6320 (2006).
Fivash, et al., "BIAcore for macromolecular interaction", *Current Opinion on Biotechnology*, 9(1):97-101 (1998).
Geiger, et al., "RNA aptamers that bind L-arginine with sub-micromolar dissociation constants and high enantioselectivity", *Nucleic Acids Research*, 24(6)71029-1036 (1996).
Giordano, et al., "Towards dynamic coating of glass microchip chambers for amplifying DNA via the polymerase chain reaction", *Electrophoresis*, 22(2):334-340 (2001).
Gopinath, S.C.B., "Methods developed for SELEX", *Analytical and Bioanalytical Chemistry*, 387(1):171-182 (2007).
Green, et al., "Aptamers as reagents for high-throughput screening". *BioTechniques.* 30(5):1094-1110 (2001).
Hamula, et al., "Selection and analytical applications of aptamers". *Trends Anal. Chen.*, 25(7):681-691 (2006).
*Handbook of Affinity Chromatography*, 2 Edition. Edited by David S. Hage, Taylor and Francis, (Table of Contents) (2006).
Herr, et al., "Aptamer-conjugated nanoparticles for selective collection and detection of cancer cells", *Analytical Chemistry*, 78(9):2918-2924 (2006).
Hoffman, et al., "Immobilized DNA aptamers used as potent attractors for porcine endothelial precursor cells", *Journal of Biomedical Materials Research Part A*, 84A(3):614-621 (2008).
Hsing, et al., "Mirco- and nano-magnetic particles for applications in biosensing", *Electroanalysis*, 10(7-8)755-768 (2007).
Huang, et al., Integrated microfluidic system for rapid screening of CRP aptamers utilizing systematic evolution of ligands by exponential enrichment (SELEX). *Biosensors and Bioelectronics*, 25(17):1761-1766 (2010).
Hybarger, et al,, "A microfluic SELEX prototype", *Analytical and Bioanalytical Chemistry*, 384(1):191-198 (2006).
James, W., "Aptamers in the virologists' toolkit", *Journal of General Virology*, 88(8):351-364 (2007).
Jellinek, et al., "Potent 2'-amino-2'-deoxypyrimidine RNA inhibitors of basic Fibroblast growth-factor", *Biochemistry*, 34(36):11363-11372 (1995).
Jenison, et al., "High-resolution molecular discrimination by RNA", *Science*, 263(5152):1425-1429 (1994).
Jensen, et al., "Kinetics for hybridization of peptide nucleic acids (PNA) with DNA and RNA studied with the BIAcore technique", *Biochemistry*, 36(16):5072-5077 (1997).
Kanter, et al., "Cell-free production of SCFV fusion proteins: an efficient approach for personalized lymphoma vaccines", *Blood*, 109(8):3393-3399 (2007).
Kim, et al., "Solid phase capturable dideoxynucleotides for multiplex genotyping using mass spectrometry", *Nucleic Acids Research*, 30(16):e85 (2002).
Kopp, et al., "Chemical amplification: Continuous-flow PCR on a chip", *Science*, 280(5366):1046-1048 (1998).
Lai, et al., "Aptamer-based electrochemical detection of picomolar platelet-derived growth factor directly in blood serum", *Analytical Chemistry*, 79(1):229-233 (2007).
Lee, et al., "A therapeutic aptamer inhibits angiogenesis by specifically targeting the heparin binding domain of VEGF $_{165}$", *PNAS*, 102(52):18902-18907 (2005).
Lermo, et al., "In-situ DNA amplification with magnetic primers for the electrochemical detection of food pathogens", *Biosensors and Bioelectronics*, 22(9-10):2010-2017 (2007).
Lin, et al., "Aptamer-Based Microfluidic Biosensors", *9th IEEE Conference on Nanotechnology*, pp. 812-814 (2009).
Liu, et al., "Micro air bubble formation and its control during polymerase chain reaction (PCR) in polydimethylsiloxane (PDMS) microreactos", *Journal of Micromechanics and Microengineering*, 17:2055-2064 (2007).
Lowe, et al., "Multiplex single nucleotide polymorphism genotyping utilizing ligase detection reaction coupled surface enhanced raman spectroscopy", *Analytical Chemistry*, 82(13):5810-5814 (2010).
Lupold, et al., "Identification and characterization of nuclease-stabilized RNA molecules that bind human prostate cancer cells via the prostate-specific membrane antigen", *Cancer Research*, 62(14):4029-4033 (2002).
Mannironi, et al,, "In vitro selection of dopamine RNA ligands", *Biochemistry*, 36(32):9726-9734 (1997).
Mendonsa, et al., "In-vitro evolution of functional DNA using capillary electrophoresis", *Journal of the American Chemical Society*, 126(1):20-21 (2004).
Miltenyi, et al., "High gradient magnetic cell separation with MACS", *Cytometry Part A.*, 11(2):231-238 (1990).
Misra, et al.. "Microbead device for isolating biotinylated oligonucleotides for use in mass spectrometric analysis", *Analytical Biochemistry*, 384(1):96-100 (2009).
Mosing, et al., "Capillary electrophoresis-SELEX selection of aptamers with affinity for HIV-1 reverse transcriptase", *Anal. Chem.*, 77(19):6107-6112 (2005).
Murphy, et al., "An improved method for the in vitro evolution of aptamers and applications in protein detection and purification", *Nucleic Acids Research*, 31(18):e110 (2003).
Nieuwlandt, et al., "In-vitro selection of RNA ligands to substance-P", *Biochemistry*, 34(16):5651-5659 (1995).
Nimjee, et al., "The potential of aptamers as anticoagulants", *Trends Cardiovascular Medicine*, 15(1):41-45 (2005).
O'Sullivan, et al., "Aptasensors—the future of biosensings", *Analytical and Bioanalytical Chemistry*, 372:44-48 (2002).
Prosek, et al., "Aptamers-basic research, drug development, and clinical applications", *Appl. Microbiol. Biotechnol.*, 69:367-374 (2005).
Ramsey, et al., "Integrated microfluidic device for solid-phase extraction coupled to micellar electrokinetic chromatography separation", *Anal. Chem.*, 77:6664-6670 (2005).
Ravelet, et al., "Liquid chromatography, electrochromatography, and capillary electrophoresis applications of DNA and RNA aptamers", *Journal of Chromatogrraphy A*, 1117:1-10 (2006).

(56) References Cited

OTHER PUBLICATIONS

Reigstad, et al., "Platelet-derived growth factor (PDGF)-C, a PDGF family member with a vascular endothelial growth factor-like structure", *The Journal of Biological Chemistry*, 278(19):17114-17120 (2003).

Reuter, et al., "Kinetics of protein-release by an aptamer-based DNA nanodevice", *European Physical Journal E.*, 22(1):33-40 (2007).

Romig, et al., "Aptamer affinity chromatography: combinatorial chemistry applied to protein purification", *Journal of Chromatography B—Analytical Technologies in the Biomedical and Life Sciences*, 731(2):275-284 (1999).

Shamah, et al., "Complex target SELEX", *Accounts of Chemical Research*, 41(1): 130-138 (2008).

Shangguan, et al., "Cell-specific aptamer probes for membrane protein elucidation in cancer cells", *Journal of Proteame Research*, 7(5):2133-2139 (2008).

Shao, et al., "Emulsion PCR: A high efficient way of PCR amplification of random DNA libraries in aptamer selection", *PlosOne*, 6(9):E24910 (2011).

Sikavitsas, et al., "Transport and kinetic processes underlying biomolecular interactions in the BIACORE optical biosensor", *Biotechnology Progress*, 18(4):885-897 (2002).

So, et al., "Detection and titer estimation of *Escherichia coli* using aptamer-functionalized single-walled carbon-nanotube field-effect transistors", *Small*, 4(2):197-201 (2008).

Stroock, et al., "Controlling flows in microchannels with patterned surface charge and topography", *Accounts of Chemical Research*, 36(8):597-604 (2003).

Tang, et al., Chip-based genotyping by mass spectrometry, *PNAS*, 96(18):10016-10020 (1999).

Taylor, et al., "Dynamics of an anti-VEGF DNA aptamer: A single-molecule study", *Biochemical and Biophysical Research Communications*, 373(2):213-218 (2008).

Temples, et al., "On-line coupling of size exclusion chromatography and capillary electrophoresis via solid-phase extraction and a Tee-split interlace", *Journal of Chromatography B*, 839:30-35 (2006).

Thorsen, et al., "Microfluidic large-scale integration", *Science*, 298 (5593):580-584 (2002).

Tombelli, et al., "Analytical applications of aptamers", *Biosensors and Bioelectronics*, 20:2424-2434 (2005).

Toriello, et al., "Integrated affinity capture, purification, and capillary electrophoresis microdevice for quantitative double-stranded DNA analysis", *Anal. Chem.*, 79(22):8549-8556 (2007).

Tuerk, et al., "Systematic evolution of ligands by exponential enrichment: RNA ligands to bacteriophage T4 DNA polymerase", *Science*, 249:505-510 (1990).

Unger, et al., "Monolithic microfabricated valves and pumps by multilayered soft lithography", *Science*, 288:113-116 (2000).

Viskari, et al., "Unconventional detection methods for microfluidic devices", *Electrophoresis*, 27(9):1797-1810 (2006).

Wallis, et al., "Vasopressin is a physiological substrate for the insulin-regulated aminopeptidase IRAP", *Am. J. Physiol. Endocrinol. Metab.*, 293(4): E1092-E1102 (2007).

Wang, et al., "Demonstration of MEMS-based differential scanning calorimetry for determining thermodynamic properties of biomolecules", *Sensors and Actuators B: Chemical*, 134:953-958 (2008).

Wang, et al., "Pre-binding dynamic range and sensitivity enhancement for immuno-sensor using nanofluidic preconcentrator", *Lab on a Chip*, 8:392-394 (2007).

Williams, et al., "Bioactive and nuclease-resistant $_L$-DNA ligand of vasopressin", *PNAS*, 94(21):11285-11290 (1997).

Wu, et al., "MEMS flow sensors for nano-fluidic applications", *Sensors and Actuators A.*, 89(1-2):152-158 (2001).

Xia, et al., "Chaotic micromixers using two-layer crossing channels to exhibit fast mixing at low Reynolds numbers", *Lab on a chip*, 5(7):748-755 (2005).

Xiaoyu, et al., "Polydimethylsiloxane (PDMS)-based spiral channel PCR chip", *Electronics Letters*, 46(16):890-891 (2005).

Yang, et al., "Advances in SELEX and application of aptamers in the central nervous system", *Biomolecular Engineering*, 24(6):583-592 (2007).

Yang, et al., "DNA ligands that bind tightly and selectively to cellobiose", *PNAS*, 95(10):5462-5467 (1998).

Yeung, et al., "A DNA biochip for on-the-spot multiplexed pathogen identification", *Nucleic Acids Res.*, 34(18):e118 (2006).

Yu, et al., "Preparation of monolithic polymers with controlled porous properties for microfluidic chip applications using photoinitiated free-radical polymerization", *Journal of Polymer Science Part A-Polymer Chemistry*, 40(6):755-169 (2002).

Zhang, et al., "In-vitro selection of bacteriophage ø 29 prohead RNA aptamers for prohead binding", *The Journal of Biological Chemistry.*, 273(5)2947-2953 (1998).

Zhang, et al., "Differentiation and detection of PDGF isomers and their receptors by tunable aptamer capillary electrophoresis", *Analytical Chemistry*, 81(18):7795-7800 (2009).

International Search Report and Written Opinion for PCT/US2012/056888, dated Feb. 25, 2013.

International Search Report and Written Opinion for PCT/US2012/056926, dated Dec. 3, 2012.

Sanchez-Freire et al., "Microfluidic single-cell real-time PCR for comparative analysis of gene expression patterns", Nature Protocols, 7:829-838 (Apr. 2012).

White et al., "High-throughput microfluidic single-cell RT-qPCR", PNAS, 108(34):13999-14004 (Aug. 2011).

Stahlberg et al., "Single-cell gene-expression profiling and its potential diagnostic applications", Exp. Rev. of Mol. Diagnostics, 11(7):735-740 (Sep. 2011).

U.S. Appl. No. 14/221,596, filed Mar. 21, 2014.

U.S. Appl. No. 14/223,767, filed Mar. 24, 2014.

Jayasena, "Aptamers: An emerging class of molecules that rival antibodies in diagnostics", *Clinical Chemistry*, 45(9):1628-1650 (1999).

U.S. Appl. No. 12/568,651, filed Dec. 31, 2012 Notice of Abandonment.

U.S. Appl. No. 12/568,651, filed Apr. 13, 2012 Final Office Action.

U.S. Appl. No. 12/568;651, filed Mar. 12, 2012 Response to Non-Final Office Action.

U.S. Appl. No. 12/568,651, filed Sep. 12, 2011 Non-Final Office Action.

U.S. Appl. No. 13/652,214, filed May 28, 2014 Non-Final Office Action.

International Search Report and Written Opinion for PCT/US2013/070075, dated Feb. 21, 2014.

Xu et al., "Review: Aptamers in microfluidic chips", *Analytica Chimica Acta*, 683(1):12-20 (2010).

Chen et al., "An automatic microfluidic system that continuously performs the systematic evolution of ligands by exponential enrichment", *Microfluidics and Nanofluidics*, 13(6):929-939 (2012).

Kim et al., "A microchip for nucleic acid isolation and enrichment", *2012 IEEE 25th International Conference on Micro Electro Mechanical Systems*, pp. 765-768 (2012).

Ahn et al., "A sol-gel-based microfluidics system enhances the efficiency of RNA aptamer selection", *Oligonucleotides*, 21(2):93-100 (2011).

\* cited by examiner

SYSTEMS AND METHODS FOR THE CAPTURE AND SEPARATION OF MICROPARTICLES

RELATED APPLICATIONS

The present application claims priority to U.S. Provisional Application Ser. No. 61/171,331, filed on Apr. 21, 2009, the disclosure of which is incorporated by reference herein in its entirety.

STATEMENTS OF REGARDING FEDERALLY SPONSORED RESEARCH OR DEVELOPMENT

The subject matter disclosed herein was developed with government support under National Science Foundation grant numbers CCR-0325344, DBI-0650020, and CBET 0854030, and the National Institutes of Health grant number RR025816-01A1. The government has certain rights in the disclosed subject matter.

BACKGROUND

Microfluidic particle separation is widely used in sorting, purification, enrichment and detection of cells in cell biology, drug discovery, and clinical diagnostics. A number of methods currently exist for particle separation on microfluidic platforms, such as size-based separation, acoustic separation, dielectrophoresis, fluorescence-activated and magnetic-activated separation. Among these, methods based on magnetic control are particularly attractive. These methods utilize surface-functionalized magnetic beads to capture target microparticles and to separate the target microparticles by magnetic manipulation. This separation scheme can be based on specific binding between the magnetic beads and the target microparticles instead of relying on geometrical or physical properties of the particles, and hence allows highly specific and selective particle separation.

There are two well known operating modes for magnetically based microfluidic particle separation: batch mode and continuous flow mode. In the batch mode, target-bound magnetic beads are retained on a solid surface, and subsequently released following the removal of non-target microparticles with a liquid phase. Magnetic bead beds and sifts have for example been developed for this purpose, but have limited separation efficiency. A number of devices have been attempted to address this issue with various magnet designs, including a quadruple electromagnet, a planar electromagnet, or nickel posts. In addition, planar electromagnets can be integrated on chip with microvalves and micropumps to enable fully automated functionalities such as fluid actuation and particle mixing. Many batch-mode designs suffer from several inherent limitations including prolonged durations of operation, complicated fluidic handling, and contamination due to non-specific trapping of impurities that are sequestered in the beads.

These limitations can be mitigated by continuous-flow magnetic bead separation, which employs magnetic fractionation, i.e., continuous accumulative deflection of magnetic beads. This method can be classified into two categories depending on whether an integrated magnet or off-chip magnet is used. In the first category, magnetic microstrips of alloy or ferromagnetic materials are deposited on the device substrate for generating a magnetic field gradient to separate magnetic beads. However, this on-chip integrated magnet microstrip design typically requires sophisticated design and fabrication to achieve a proper balance between hydrodynamic and magnetic forces. Alternatively, the use of a simple external magnetic setup in conjunction with on-chip separation allows greater flexibility in device design and magnetic manipulation. In either case, however, magnetic separators can be limited by prolonged off-chip incubation of target microparticles with magnetic beads, which is used to ensure sufficient bead-particle interaction and binding before on-chip separation. This off-chip incubation is time-consuming, labor-intensive, and prone to contamination, and in the case of cell separation could compromise the viability of target cells.

There exists a need to provide simple yet effective on-chip magnetically based systems and methods for capturing and separating target microparticles.

SUMMARY

This presently disclosed subject matter provides techniques for capturing and isolating target microparticles based on magnetic manipulation.

In one aspect, the disclosed subject matter provides a method for capturing target microparticles, the method including: forming a fluid including the target microparticles, non-target microparticles, and magnetic beads, the magnetic beads having a stronger affinity with the target microparticles than with the non-target microparticles, flowing the fluid through a multidirectional microchannel; and applying a magnetic field to the fluid while the fluid is flowing through at least a portion of the microchannel to effect capture of at least a portion of the target microparticles onto the magnetic beads.

In some embodiments of the above method, the microchannel is substantially planar. In some embodiments, the microchannel has a width between 100 µm and 200 µm.

In some embodiments of the above method, the microchannel a serpentine shaped microchannel having a plurality of straight segments. In certain embodiments, each of the plurality of straight segments of the serpentine shaped microchannel is substantially perpendicular to the magnetic field.

In some embodiments of the above method, applying the magnetic field comprises placing a permanent magnet near the microchannel. In such embodiments, the microchannel can have a width which increases as the multidirectional microchannel extends away from the permanent magnet.

In some embodiments of the above method, the target particles can comprise bacteria, viruses, micelles, polypeptides, nucleic acids, biological cells, or particles coated with ligands, polypeptides or nucleic acids. In one embodiments, the target particles comprise cancerous leukocytes.

In other embodiments, the magnetic beads comprise a functional group that can be a nucleic acid aptamer, a peptide, a small molecule ligand, and an antibody. In one embodiment, the magnetic beads comprise at least one antibody. The target microparticles can comprise microparticles having an average size of 5 µm to 20 µm.

In another aspect, the disclosed subject matter provides a method for isolating target microparticles, which includes: forming a fluid including the target microparticles, non-target microparticles, and magnetic beads, the magnetic beads having a stronger affinity with the target microparticles than with the non-target microparticles; flowing the fluid through a multidirectional microchannel; applying a first magnetic field to the fluid while the fluid is flowing through at least a portion of the microchannel to effect capture of at least a portion of the target microparticles onto the magnetic beads; and passing the fluid having exited from the microchannel through a separator while subjecting the fluid to a second magnetic field so as to isolate the target microparticles. In some embodiments of this method, the microchannel through which the fluid flows is serpentine shaped having a plurality of straight segments. In some embodiments, the first magnetic field and the second magnetic field are produced by a same magnet.

In yet another aspect, the disclosed subject matter provides a device for capturing and/or isolating target microparticles from a fluid. The fluid comprises the target microparticles, non-target microparticles, and magnetic beads having a stronger affinity with the target microparticles than with the non-target microparticles. The device includes a multidirectional microchannel adapted to permit the fluid to flow through, and one or more magnets positioned such that a magnetic field is applied to the fluid while the fluid is flowing through at least a portion of the microchannel, to thereby effect capture of at least a portion of the target microparticles onto the magnetic beads.

In some embodiments, the device further comprises a first inlet coupled to the microchannel for introducing the target microparticles and non-target microparticles into the microchannel, and a second inlet coupled to the microchannel for introducing a suspension including the magnetic beads into the microchannel.

In some embodiments, the device further comprises a separator portion which is fluidically coupled with the microchannel and configured to isolate the target microparticles from the fluid. In such embodiments, the separator portion can further comprise a buffer inlet for introducing a buffer to the fluid so as to isolate the target particles. Further, the device can comprise a target microparticle collection outlet coupled to the separator portion for collecting magnetic beads-bound target microparticles.

In some embodiments, the separator portion of the device is formed on the same substrate as the microchannel.

BRIEF DESCRIPTION OF THE DRAWINGS

For a more complete understanding of example embodiments of the described subject matter and its advantages, reference is now made to the following description, taken in conjunction with the accompanying drawings, in which.

DETAILED DESCRIPTION

The disclosed subject matter provides techniques for capturing and/or isolating target microparticles in a sample. The techniques include using a magnetic field to manipulate a fluid comprising magnetic particles and target microparticles flowing in a microchannel to selectively capture target microparticles, and to separate such captured microparticles from unwanted particles in the sample. The disclosed subject matter further provides microfluidic devices and systems for accomplishing target microparticles capture and isolation.

Figure 1:
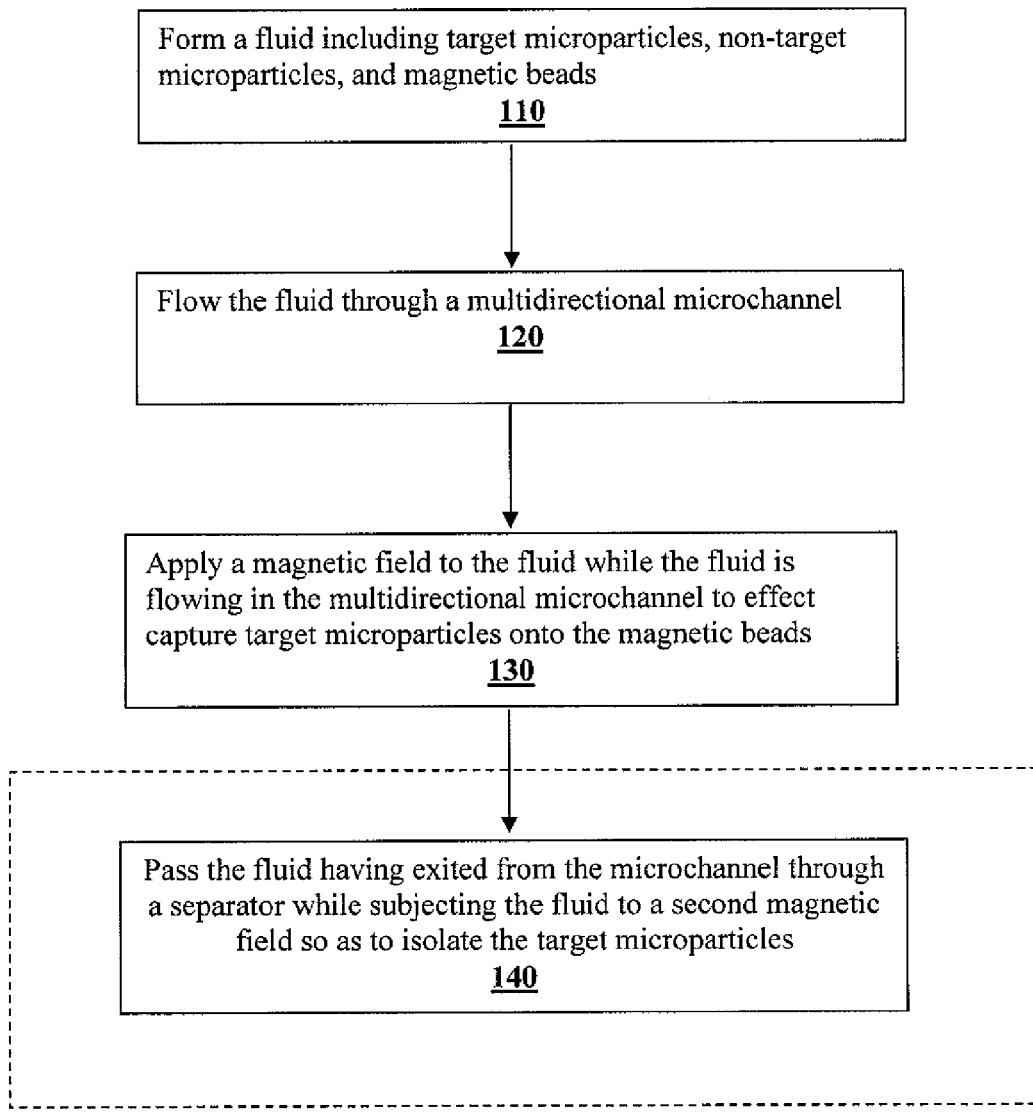
FIG. 1 depicts a block diagram illustrating a method for capturing and/or isolating target microparticles according to some embodiments of the disclosed subject matter.

Referring to FIG. 1, a method for capturing target microparticles is described. At 110, a fluid is formed including the target microparticles, non-target microparticles, and magnetic beads, the magnetic beads having a stronger affinity with the target microparticles than with the non-target microparticles. Then, at 120, the fluid is flowed through a continuous multidirectional microchannel. At 130, while the fluid is flowing through at least a portion of the microchannel, a magnetic field is applied to the fluid to effect capture of at least a portion of the target microparticles onto the magnetic beads.

The disclosed subject matter also provides techniques for isolating target microparticles which includes the above procedures for capturing the target microparticles. At 140, the now exited fluid can be passed through a separator while being subjected to a second magnetic field so as to isolate the target microparticles.

The disclosed subject matter provides continuous and automatic on-chip capture (or incubation) of target microparticles in a fluid by magnetic particles, which differ from traditional approaches requiring bulk fluid mixing. Such capture can be carried out in an incubator portion, which includes a multidirectional microchannel through which the fluid travels. An exemplary incubator is designed based on a scheme termed herein as target acquisition by repetitive traversal (TART), in which surface-functionalized magnetic beads specifically bind with target microparticles by repetitively traversing the fluid containing the target microparticles. This is accomplished by a combination of an on-chip multidirectional microchannel geometry and an applied magnetic field. The described techniques also include an example where the incubator portion and the separator portion are integrated on a single chip (or formed on a single substrate).

Figure 2:
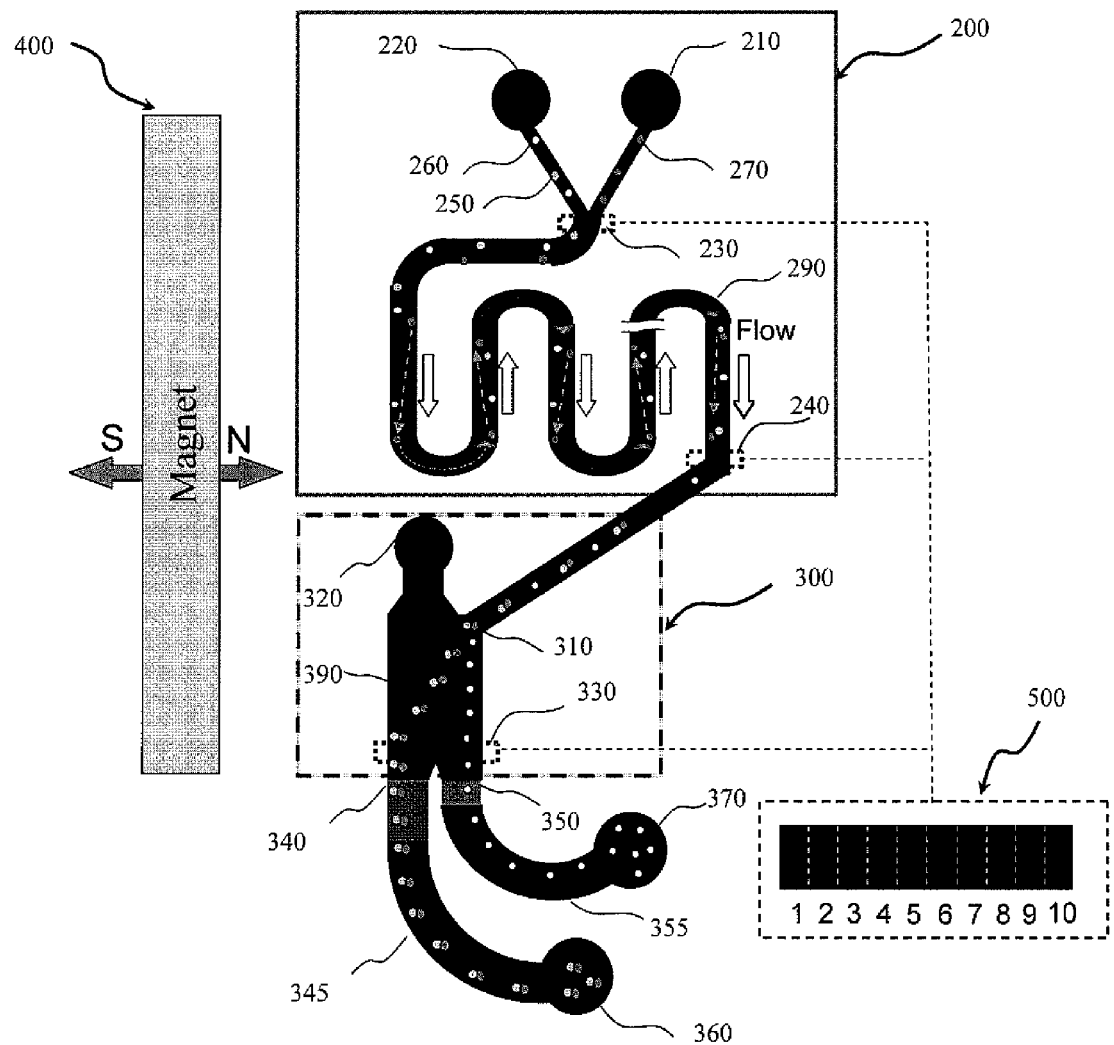
FIG. 2 depicts a schematic diagram of a system for capturing and/or isolating target microparticles according to some embodiments of the disclosed subject matter.

FIG. 2 depicts a schematic diagram illustrating the described techniques. A microfluidic system includes an incubator portion 200 and separator portion 300, where the separator portion is fluidically coupled to the incubator portion. A sample presented to the microfluidic system can be a mixture of target microparticles 250 and non-target microparticles 260, which differ in their respective affinity toward the magnetic particles 270. The sample and magnetic beads can be fed into the microchannel portion 290 through separate inlets, e.g., inlet 220 for the sample and inlet 210 for the magnetic beads. The fluid streams containing the sample and the magnetic beads merge at the Y-shaped junction 230, where the fluid streams before merging can be controlled by separate mechanisms, i.e., syringe pumps, to adjust the respective flow rates. The incubator portion and separator portion can be placed near a magnetic source 400, e.g., a permanent magnet or electromagnet providing a magnetic gradient. Particle distributions can be analyzed, e.g., based on fluorescence spectroscopy, in the observation regions at or slightly below the Y-junction 230, the end (or the exit) 240 of the incubator portion, and near the end of the separator portion 330. These regions can be each divided into 10 lanes (by the dotted imaginary lines shown in the template 500) to facilitate analysis.

As used herein, the term "target microparticles" refers to microparticle species of interest that is the target of the capture and/or isolation procedures. The magnetic beads used have higher affinity with the target microparticles than with the non-target microparticles. Embodiments of target microparticles can include without limitation, bacteria, viruses, micelles, polypeptides, nucleic acids, particles coated with a ligand, polypeptide or nucleic acid, biological cells including, e.g., white and red blood cells, and certain cancer cells. Examples of the cancer cells include cancerous leukemia cells (or leucocytes) (e.g., CCRF-CEM, Toledo, Ramos, Raji, etc.) or migrating cancerous cells such as liver cancer cells, which may appear in lymph system during metastasis. The average size in diameter of target microparticles can vary depending on the chemical composition and structure of the target microparticles, and can be, for example, 0.05 µm to 100 µm, 0.1 µm to 15 µm, 5 to 20 µm, or 0.5 µm to 5 µm.

As used herein, the term "non-target microparticles" refers to particles species that have lower affinity with the magnetic beads, as compared to the target microparticles. Non-target microparticles can be of similar or different size, have functional groups, or other characteristics as the target microparticles. Non-target microparticles can include any unwanted species in the sample including target microparticles, for example, impurities in the sample, or the solvent in which the target microparticles are suspended, e.g., water.

Magnetic beads as used in the currently disclosed subject matter are beads containing a core of a magnetic material which is attracted to a magnet. The magnetic material can be either paramagnetic or ferromagnetic. The surface of the magnetic beads can be functionalized to contain a wide variety of chemical groups suitable for binding and/or capturing target microparticles. For example, the functional groups on the magnetic beads can be nucleic acid aptamers, peptides, small molecule ligands, antibodies, among others, that specifically bind with the target microparticles based on molecular recognition. The affinity-based binding between the magnetic beads and the target microparticles is also referred to as incubation. The suitable average size in diameter of the magnetic beads can depend on the strength and the placement of the source of the magnetic field, e.g., a magnet, as well as on the dimension and geometry of the microchannel through which the fluid flows through. See Verpoorte, "Beads and chips: new recipes for analysis," Lab Chip, 2003, 3, 60N-68N, which is incorporated herein by reference.

In the TART incubation scheme, a sample and magnetic bead suspension flow in a multidirectional microchannel, where the magnetic beads repetitively traverse the sample stream to seek out and capture target microparticles. As shown in FIG. 2, the sample and magnetic bead suspension are introduced through their respective inlets 220 and 210, merge at a Y-junction, and then enter the microchannel 290. As used herein, a "multidirectional microchannel" refers to a channel that continuously or repetitively changes the flow direction of a fluid it contains relative to the direction of the magnetic field such that the magnetic particles in the fluid have repetitive transverse motions relative to the direction of fluid flow. For example, the multidirectional microchannel can include a plurality of a first section, wherein each of two adjacent first sections are connected by a turn such that the two adjacent first sections have alternating directions with respect to a reference direction, e.g., with respect to the direction of the gradient of the magnetic field.

The multidirectional microchannel can take a variety of shapes, for example, periodic curves like sine waves, serpentine shape including a series of straight sections substantially parallel to one another, with the neighboring two straight sections connected by U-shaped turns. The microchannel can be corner-free, e.g., when it takes a serpentine shape, in which case the incubator can have zero dead volume. This reduces undesired particle or magnetic-bead retention. The microchannel can be substantially planar, for example, the aspect ratio of the channel cross section (depth:width) ranges from 1:3 to 1:30, and fabricated using soft lithography techniques on a substrate for the desired dimension and shape. With a planar design, the microfluidic device including the incubator and separator portions can be fabricated with a straightforward one-mask soft lithography process. Thus, such a device can be of great utility for isolation and analysis of micro/nanoparticles and cells in lab-on-a-chip systems. For example, it can be used in point-of-care settings for tests of cancer and autoimmune disease, among others.

The dimension of the microchannel can have a width ranging from 50 µm to 500 µm, or alternatively 100 µm to 200 µm. This small dimension dictates that the fluid flow behavior in low Reynolds number condition, which allows the sample and magnetic bead suspension to flow side by side as two laminar streams throughout the incubation channel. In the absence of a magnetic field, target and non-target microparticles as well as magnetic beads would also remain in their respective fluid streams with negligible lateral diffusion. Using the serpentine-shaped microchannel for illustration below, with the lateral magnetic field generated by the magnet in the straight channel sections, magnetic beads are pulled toward the magnet (i.e., to the left in FIG. 2). Thus, the beads, initially located in the right-side stream in the leftmost straight section of the incubation channel, deflect to the left and cross the flow streamlines. Immediately after passing the first U-turn, the magnetic beads follow the streamlines and emerge again on the right side when entering the next straight channel section. In the subsequent sections downstream, this process is repeated with the beads alternately shuttled between the left and right. This repetitive lateral traversal of magnetic beads in the sample stream allows the beads to effectively seek out and capture target microparticles. The number of turns, or the contour length of the microchannel can be determined by the identity of the target microparticles, the functional groups on the magnetic beads, the strength of the magnet used, the desired incubation efficiency, among other factors.

Still using the serpentine channel configuration for illustration, the magnetic pulling force experienced by magnetic beads in general varies with the distance of the straight channel sections from the magnet. To address this issue and allow for consistent traversal of magnetic beads in the incubation channel sections, the incubator design can employ straight channel sections whose widths are proportional to their distance from the permanent magnet. Given flow continuity, such a design allows reduced flow speeds and longer residence times in the channel sections at farther distances from the magnet to compensate for the weakened magnetic force therein. This effectively reduces undesired particle retention in the upstream channel sections (which are closer to the magnet) and ensures adequate bead deflection in the downstream sections (which are relatively further away from the magnet).

After the bead-captured target microparticles emerge from the incubator portion and enter the separator portion, they are isolated from the non-target microparticles by magnetic fractionation in the separator portion (FIG. 2). The separator can include an additional inlet 320, referred to as the buffer inlet, which merges with the separator entrance to form a wide straight channel section. A stream of pure buffer (free of particles and beads) can be introduced into the buffer inlet and combines with the mixture of bead-captured target microparticles and non-target microparticles that has just exited the incubator. Note that the mixture can also include a small number of uncaptured target microparticles or unused magnetic beads; however, they do not interfere with the separation process. The buffer and mixture form two side-by-side laminar streams in the separator channel 390. An external magnetic field having a magnetic gradient substantially perpendicular to the separator channel 390 can be applied to the separator channel, for example, using the same magnet 400 as used for the incubator, or using a different magnet having a different magnetic strength. As the bead-captured target microparticles move downstream in the separator channel 390, the bead-bound target microparticles can be deflected by the magnetic field, for example, driven towards the magnet 400, thereby crossing the buffer stream and becoming separated from the non-target microparticles that remain in the sample stream. Thus, two outlets at the end of the collection channels following the target and waste collection channels 345 and 355, respectively, referred to as the target outlet 360 and waste outlet 370, can be used to collect the bead-captured target microparticles and non-target microparticles exiting from the target microparticles exit 340 and non-target microparticles exit 350 at the bottom of the separator, respectively. The flow rate of the buffer at the buffer inlet can be adjusted to be considerably higher than that of the sample at the separator entrance 310, which facilitates the non-target microparticles to remain in the sample stream which can be constrained within a very thin layer near the right side wall of the separator channel and then completely exited out of waste outlet 370. In this manner, the bead-captured targets collected at the target outlet can be highly pure, i.e., free of non-target microparticles. This effectively addresses the limited degree of purification in most batch-mode magnetic separation processes due to the false trapping of non-target microparticles. In addition, the flow rates for the buffer and mixture streams can be selected to produce adequate hydrodynamic driving force and prevent magnetic beads from adhering to the channel walls.

EXAMPLES

The following examples are merely illustrative of the presently described subject matter and should not be considered as limiting the scope of the disclosed subject matter in any way.

Example 1

Fabrication of an Integrated Microfluidic Device Including a TART Incubator Portion and a Separator Portion A microfluidic device was made which included a sheet of poly(dimethylsiloxane) (PDMS) bonded to a glass slide. The microfluidic features were fabricated in the PDMS sheet (the substrate) using soft lithography techniques. The fabrication process began with spin-coating and patterning of a 30-μm layer of SU-8 2025 photoresist (MicroChem, MA) on a silicon wafer, which upon curing at 95° C. for 5 min on a hotplate formed a master defining the negative of the desired microfluidic features. Next, a PDMS prepolymer (Sylgard 184, Dow Corning, MI) was cast against the master and cured at 70° C. for 35 min, also on the hotplate. The resulting PDMS sheet was then peeled off from the master, cut into suitably sized pieces, and punched with inlet and outlet holes. The PDMS was bonded to a glass slide after a 10-min treatment in a UV ozone cleaner (Model T10X10/OES, UVOCS, PA). Tygon tubes were inserted into the inlet and outlet holes in the PDMS to establish micro-to-macro fluidic interconnects.

An image of a fabricated device is shown in FIG. 3a, with ink solution filled in the channel to aid visualization. As shown, the TART incubator portion includes a microchannel having three connected blocks. The dimensions (in μm) of one such block of the TART incubator, and the dimensions (in μm) of separator are shown in FIGS. 3b and 3c, respectively. The depth of the microchannel is 30 μm for both the incubator and separator.

Example 2

Capturing and Isolating Target Microparticles Using the Integrated Microfluidic Device Fabricated Materials used in the experiments included 5% bovine serum albumin (BSA) (Sigma-Aldrich, MO), 2.8 μm streptavidin-coated magnetic beads, 0.4 μm biotin-coated green fluorescent polystyrene particles (as target microparticles), and 0.4 μm uncoated red fluorescent polystyrene particles (as non-target microparticle) (all from Spherotech, IL). The magnetic bead diameter was chosen based on a tradeoff between the needs for reducing sedimentation and ensuring sufficient magnetically driven migration mobility of the beads. The size of polystyrene particles represented those of various bacterial cells.

Three samples were used in the experiments: a) a suspension of streptavidin-coated magnetic beads (0.5% w/v) supplemented with BSA; b) a mixture of biotin-coated particles (0.1% w/v) and uncoated particles (0.1% w/v) in suspension, supplemented with BSA (target vs. non-target ratio: 1:1); and c) a mixture of biotin-coated particles (0.05% w/v) and uncoated particles (0.5% w/v) in suspension, supplemented with BSA (target vs. non-target ratio: 1:10). Deionized water was used as running buffer supplied to the separator.

Before the experiments, the microfluidic channels were incubated with 2% BSA solution for 2 hours to block non-specific adsorption, and then flushed with deionized water. Samples and buffer were driven into appropriate inlets of the device using syringe pumps (KD210P, KD Scientific, MA, and NE-1000, New Era Pump Systems, NY). A 50 mm long bar-shaped Neodymium permanent magnet (McMaster-Carr, IL) was placed alongside the device. Bright field images of magnetic beads as well as fluorescent images of target and non-target fluorescent particles were taken using an inverted epi-fluorescent microscope (Diaphot 300, Nikon Instruments, NY), and recorded by a CCD camera (Model 190CU, Micrometrics, NH). Images were analyzed and quantitative data were extracted using ImageJ® program (available free from the website of National Institute of Health).

The concentration of magnetic beads and those of target and non-target microparticles were determined by analyzing the intensity of bright field or fluorescent images as appropriate in three rectangular regions located at the Y-junction, the end of the incubator, and the end of the separator, respectively (as discussed with respect to FIG. 2). These regions were aligned with the channel, of equal width to the channel and length 1 mm along the channel. The regions were each further divided into 10 lanes of equal width to facilitate the calculation of magnetic bead and particle distributions across the channel.

Example 3

Characterization of the TART Incubator

The efficacy of the TART scheme of the incubator portion of the microfluidic device manufactured according to Example 1 was evaluated. A permanent magnet bar was placed to the immediate left of the device. Magnetic beads were injected from the bead inlet, and a suspension of target and non-target microparticles at 1:1 ratio was injected from the sample inlet, both at a flow rate of 0.5 µL/min, corresponding to an average velocity that varied from 5.6 to 2.8 mm/s along the incubator channel (FIG. 3b). This flow rate was chosen as a trade-off between the needs to reduce the retention of magnetic beads on the channel wall and ensure sufficient traversal time of magnetic beads in the sample.

Figure 4:
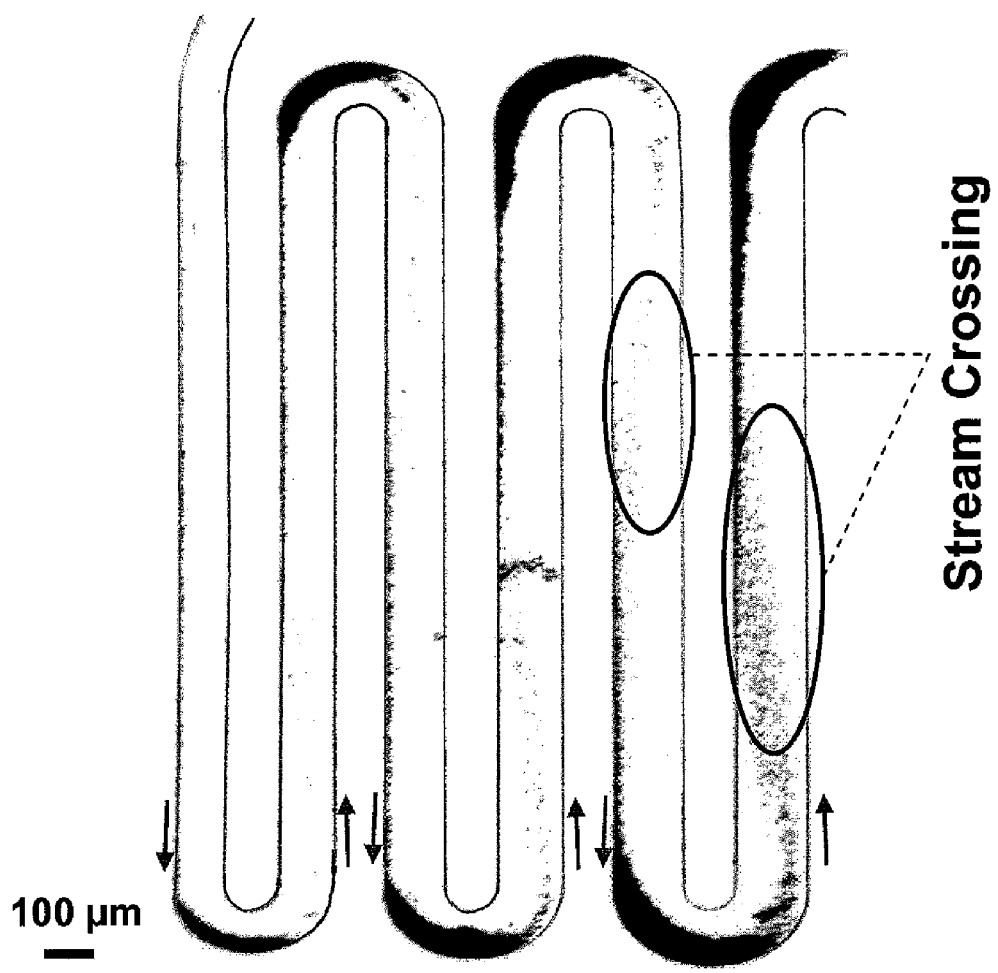
FIG. 4 depicts a micrograph image of magnetic beads migrating in the incubator according to some embodiments of the disclosed subject matter.

FIG. 4 is a snapshot image of the trajectories of magnetic beads within the TART incubator. It clearly shows that after passing each turn, magnetic beads laterally traverse the streamlines and move towards the left side of each straight channel section. This repetitive traversal of the sample by magnetic beads in the incubation channel markedly improves the contact probability and facilitates binding between the magnetic beads and the target microparticles. Although a moderate number of magnetic beads could be retained at the turns during operation, the bead inflow and outflow at the turns eventually reached equilibrium and the number of beads retained remained insufficient to cause channel clogging. Also, the retained beads observed during the experiment were easily flushed away by increasing the flow rate and/or reducing the magnetic force at the end of the operation to reduce loss of beads.

The following analysis and experimental observation can be used to further assess the role of the TART scheme in enhancing capture of target microparticles during incubation. First, there is a lack of lateral diffusion of sample particles and magnetic beads. As they travel the entire length of the incubator channel at the chosen flow rate above, the characteristic lateral diffusion distance is estimated to be about 9 µm for the target microparticles, and 2 µm for the magnetic beads. Compared with the incubator channel width (in the range of 100-200 µm) used in this study, these diffusion distances are inadequate for the effective interaction of the target microparticles and magnetic beads. Second, interactions of target microparticles and magnetic beads caused by the secondary flow in the turns of the incubator channel are negligible, as indicated by a very small Dean number, which is in the range of 0.06 to 0.12 when calculated using typical geometric and material properties. Due to the insignificance of diffusion and secondary flow, an active means of promoting the interaction of target microparticles and magnetic beads is helpful, which is offered by the TART scheme.

Figure 5:
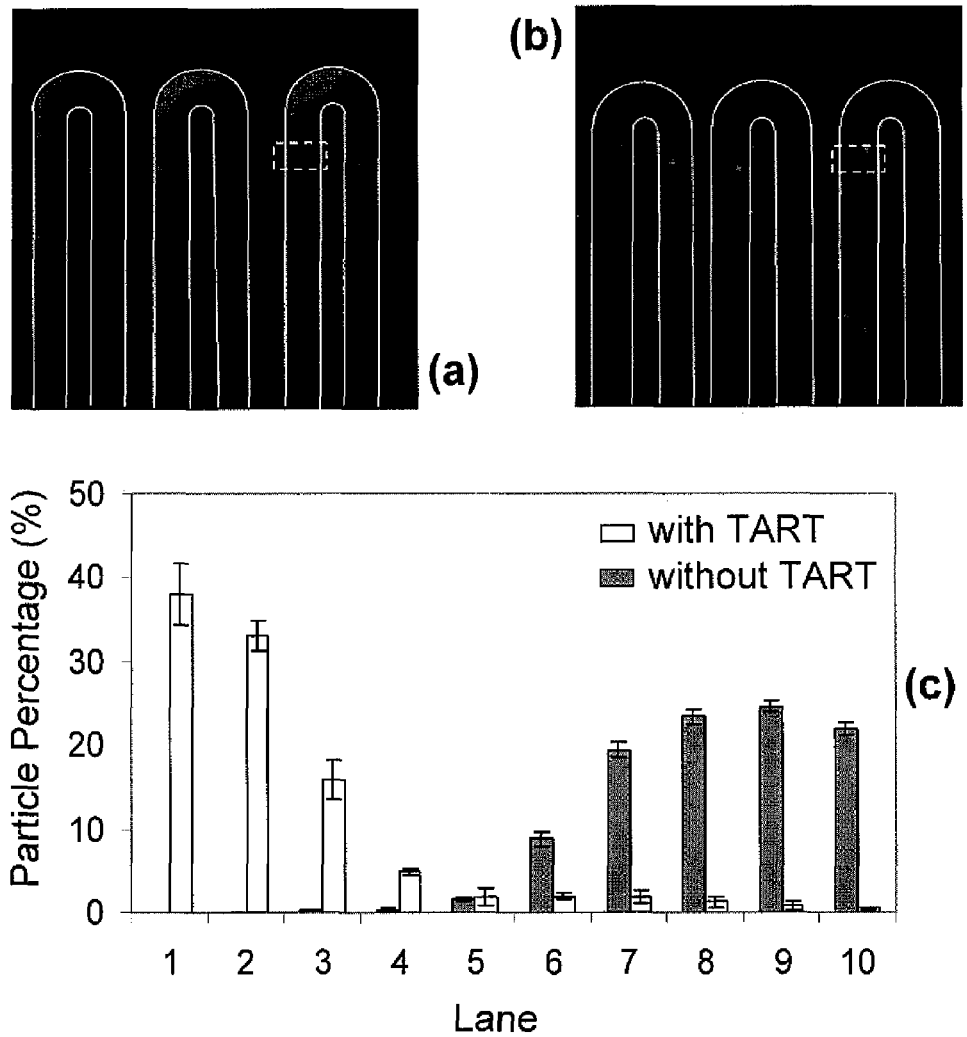
FIG. 5 illustrates a comparison of incubation in an incubator according to some embodiments of the disclosed subject matter, with and without applying the magnetic field to the incubator; (5a) Florescent image of target microparticles for incubation under an applied magnetic field applied; (5b) Florescent image of target microparticles for incubation in the absence of a magnetic field; and (5c) Percentage distributions of target microparticles across the channel width, in the dashed observation as shown in the fluorescent images.

In addition, the usefulness of the TART scheme was demonstrated by comparing the distributions of target microparticles in the incubator with and without using the TART scheme. To facilitate this comparison, the observation was made at a position immediately preceding the last turn of the microchannel (FIG. 5). When TART was enabled, i.e., when a magnetic field is applied to fluid flowing in the incubator, most target microparticles interacted with and bound to the magnetic beads, and were hence pulled towards the left channel wall. This can be seen in the concentrated distribution of target microparticles near the left channel wall (FIG. 5a). On the other hand, in the absence of an applied magnetic field, the target microparticles and magnetic beads remained in their separate laminar streams, as reflected by the fluorescence signal being limited within the sample stream (located on the right hand side of the channel, FIG. 5b). The differences between observations with and without TART are also graphed in FIG. 5c, which are significant, and indicate that the TART scheme is essential to ensuring effective capture of target microparticles by magnetic beads.

Figure 6:
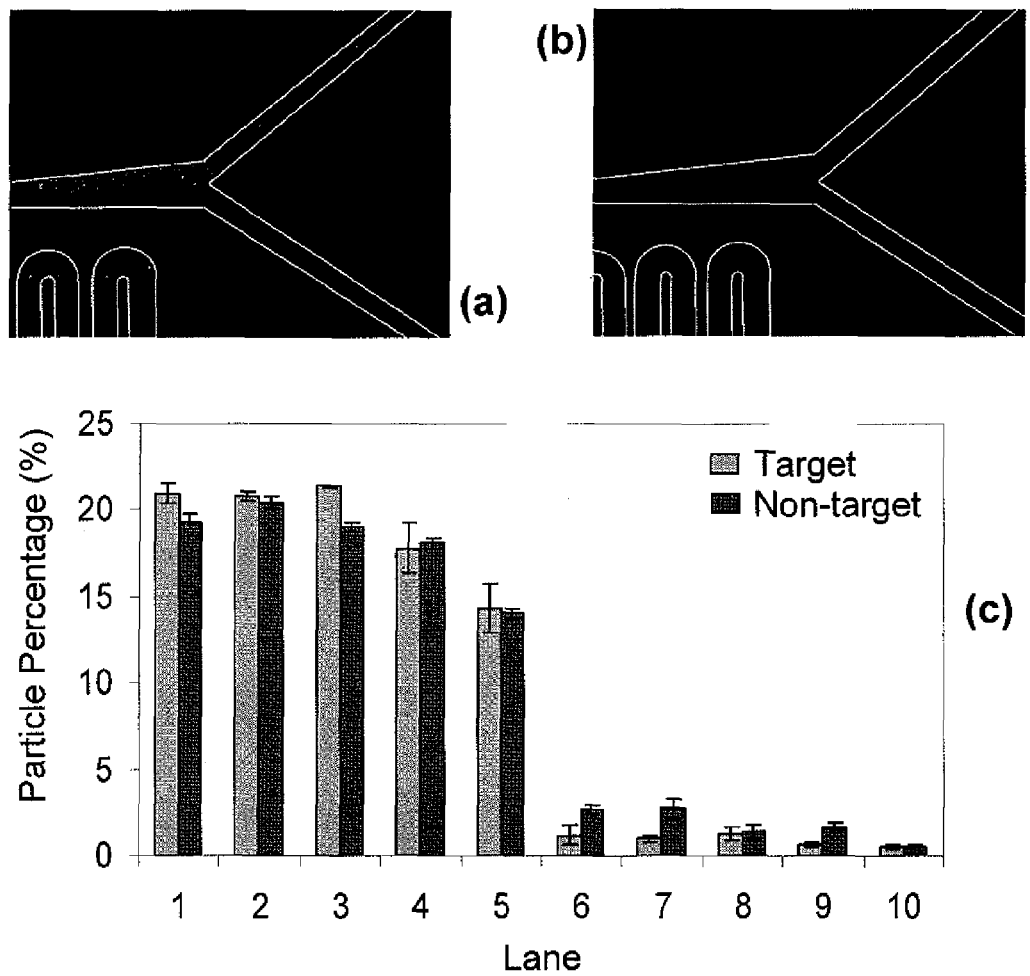
FIG. 6 depicts the distribution of target and non-target microparticles across the channel width at the Y-junction as noted in FIG. 2: (6a) Fluorescent micrographs of target microparticles at the Y-junction; (6b) Fluorescent micrographs of non-target microparticles at the Y-junction; and (6c) Percentage distributions of target and non-target microparticles across the channel width at the Y-junction.

The incubator behavior with TART was then quantitatively evaluated in terms of particle capture at the Y-junction of incubator inlets and at the incubator exit, and the differential effects of the magnetic force on the target and non-target microparticles were compared. Fluorescent images of target (green) and non-target (red) particles at the Y-junction of the incubator are shown in FIG. 6 (panels a and b, respectively). The microparticle sample and magnetic beads suspension formed two distinct, side-by-side streams, respectively, in the upper and lower halves of the Y-junction), with negligible mixing. FIG. 5c quantitatively depicts the distributions of target and non-target microparticles at the Y-junction. It can be seen that the target and non-target microparticles were both highly concentrated in Lanes 1-5, which contained over 95% of the target and the non-target microparticles, while in Lanes 6-10 the presence of target and non-target microparticles was negligible. This indicates that at the Y-junction, the particles were not mixed with the magnetic beads.

Figure 7:
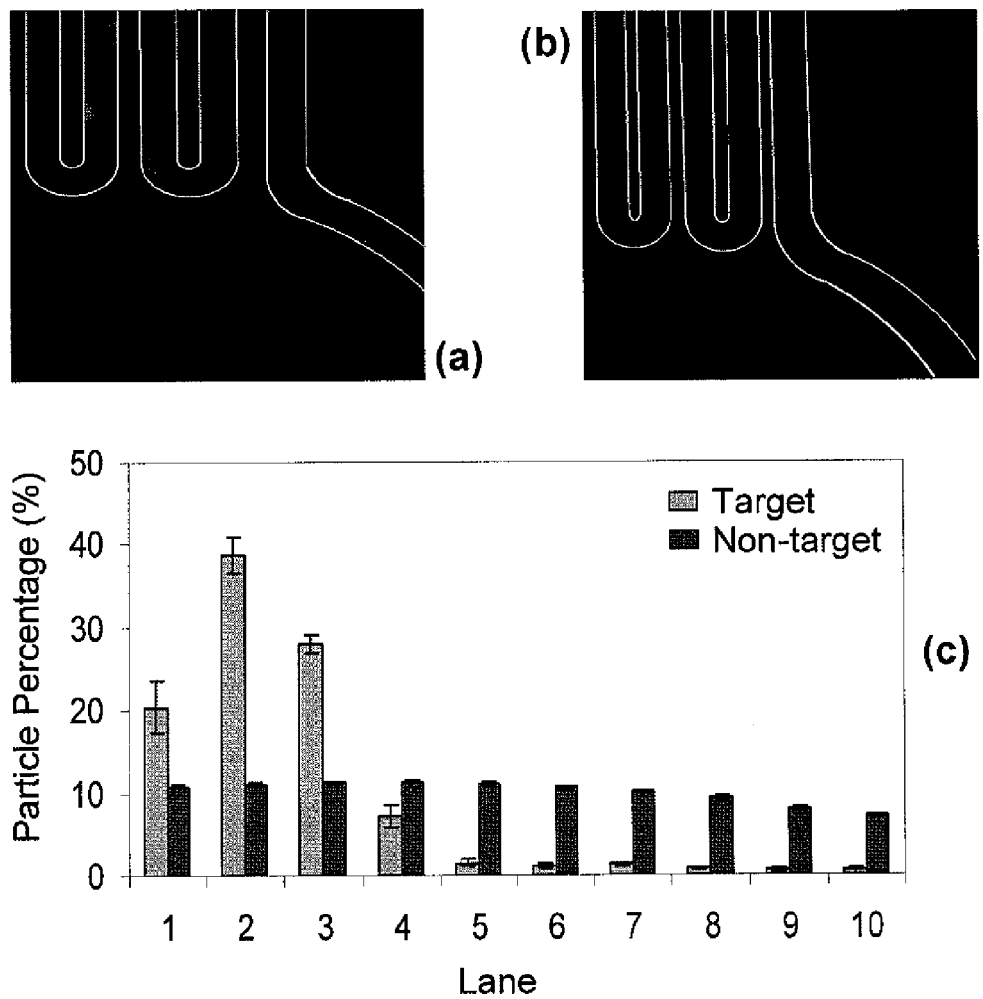
FIG. 7 depicts the distributions of target and non-target microparticles across channel width at the end of the incubator according to some embodiments of the disclosed subject matter: (7a) and (7b) Fluorescent micrographs of target and non-target microparticles, respectively, at the end of the incubator, and (7c) Percentage distributions of target and non-target microparticles across the channel width at the end of the incubator.

The particle distributions at the end of the incubator were then investigated. The fluorescent images of target (green)

and non-target (red) at the end of the incubator are given in FIGS. 7a and 7b. It can be seen that the target microparticles captured by the magnetic beads in the serpentine channel were mostly attracted to the left, where the permanent magnet is placed. On the other hand, the free non-target microparticles spread out and were distributed quite uniformly across the channel width, primarily due to flow agitation by magnetic beads in the serpentine incubation channel.

The quantitative particle distributions across the channel width at the end of the incubator are extracted and plotted in FIG. 7c. The majority of target microparticles (95.9%) appeared on the left half of the channel, whereas the non-target microparticles were evenly distributed across the channel width. The highest concentration of target microparticles did not occur in Lane 1, which can be attributed to the slight magnetization of target-bound magnetic beads and their aggregation on the left channel wall. Upon magnetization, the target-bound magnetic beads tended to aggregate into an oval-shaped cloud with tens of microns in sizes that is a few times larger than the lane width (20 µm). Therefore, when the oval cloud was attracted to the left side of the channel, Lane 1 could only probe the edge of the oval containing a small number of target microparticles, whereas the center of the oval fell in Lane 2 and included more target microparticles. The aggregation of magnetic beads also accounted for the local discontinuity in the bead suspension stream as observed.

Example 4

Characterization of the Separator

Figure 3:
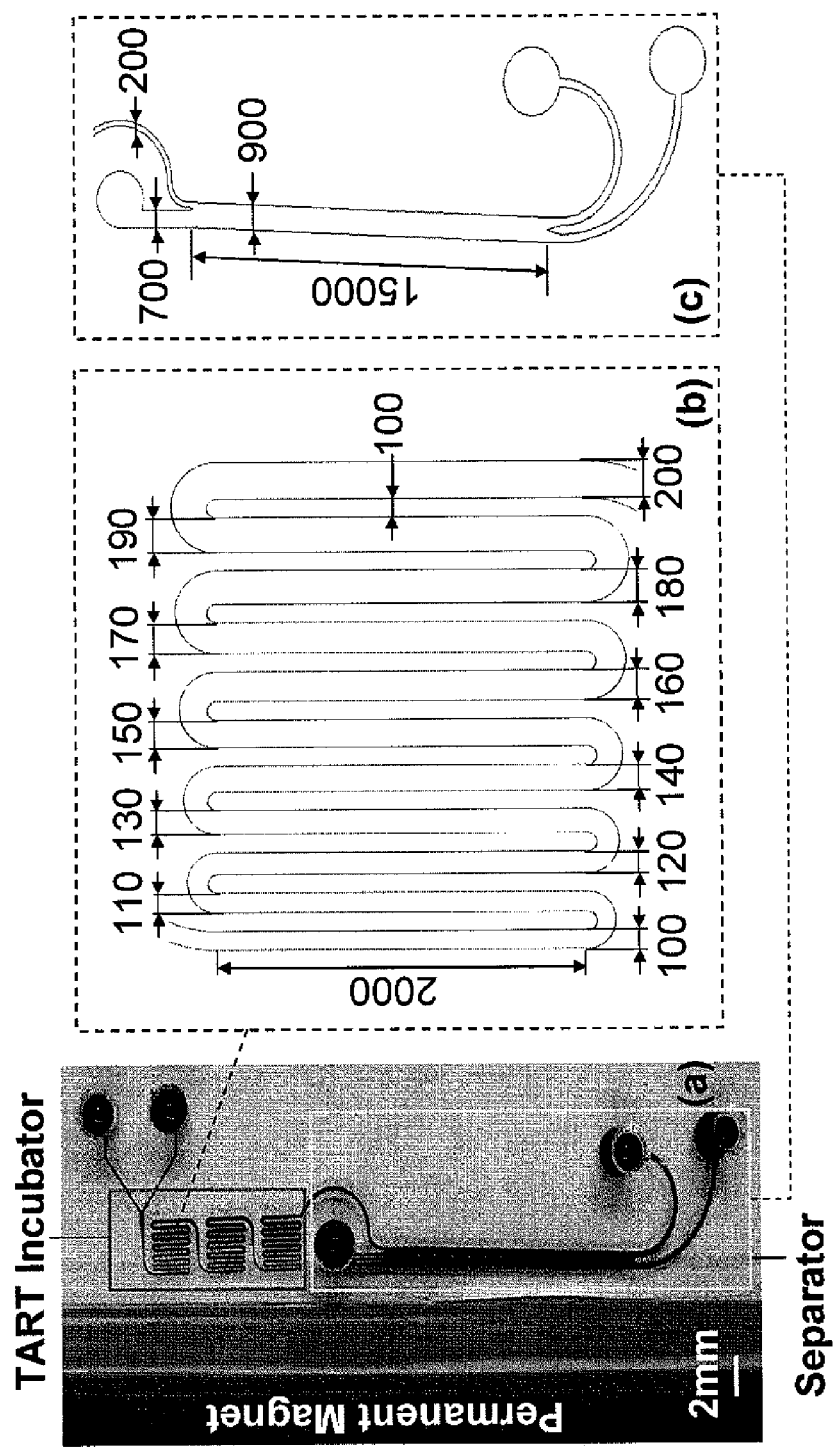
FIG. 3 depicts a photograph of a microfluidic device according to some embodiments of the disclosed subject matter (3a); dimensions (in μm) of the incubator portion of such device (3b); and dimensions (in μm) of the separator portion of the device.
Figure 8:
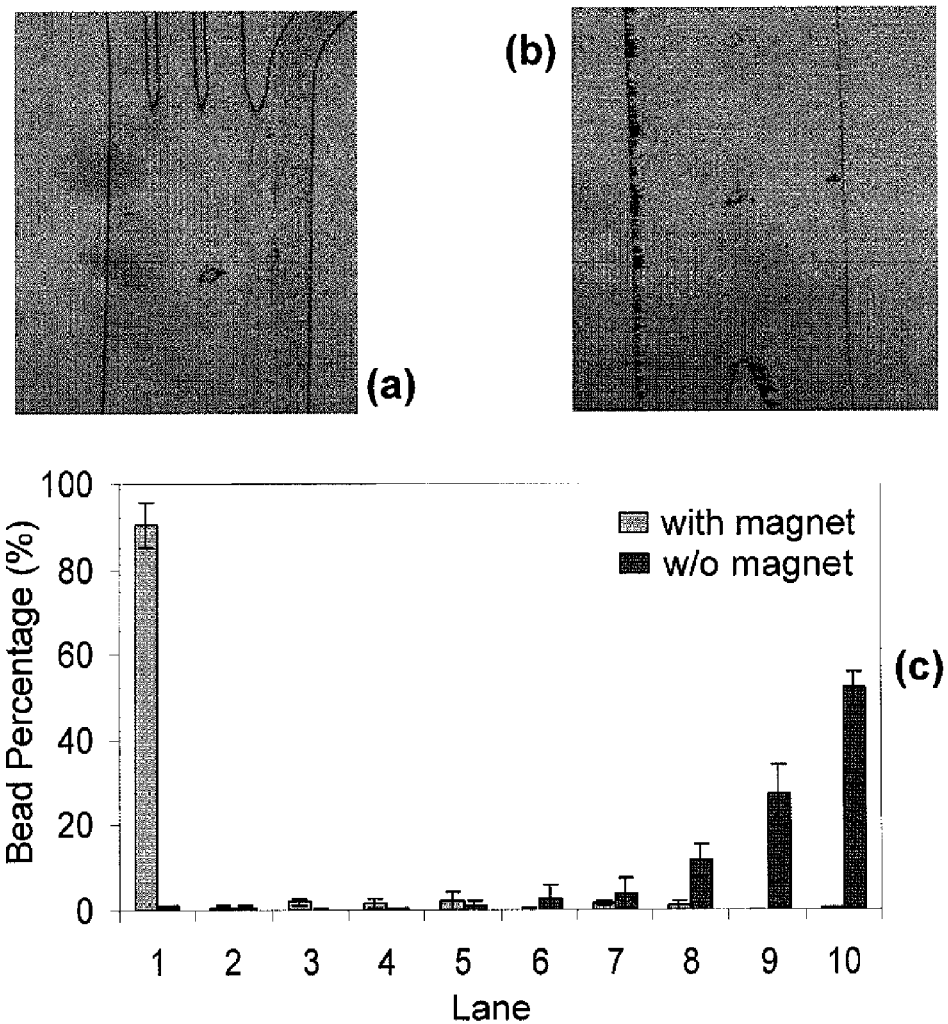
FIG. 8 illustrates control results of particle separation within a separator using bare magnetic beads: (8a) Image taken at the separator inlet (magnetic beads enter the separator from the upper right portion of the separator). (8b) Image taken at the separator exit; and (8c) Percentage distributions of magnetic beads at the separator exit.

The separator was evaluated in terms of its capacity to deflect and extract magnetic beads. For the purposes of this study, a chip was fabricated that contained exclusively the separator as shown in FIG. 3 (without a TART incubator portion). The permanent magnet was again placed to the left of the chip. A suspension of bare magnetic beads was introduced into separator entrance at a flow rate of 1 µL/min, while deionized water was introduced into the buffer inlet at 4 µL/min. As shown in FIG. 8a, when first entering the separation channel from the separator entrance, the magnetic beads were highly concentrated to the right side of the separator due to laminar flow behavior. At the exit, however, they were attracted towards the magnet and accumulate at the left-hand side (FIG. 8b).

The bead distributions across the channel width at the separator exit were compared in the cases with or without the permanent magnet. An observation region at the separator exit was selected, where the channel width was again divided into 10 lanes and the percentage of beads falling into each lane was obtained to quantify the bead distributions. As the target and waste collection channels (denoted 345 and 355, respectively, in FIG. 2) have similar hydrodynamic resistances, magnetic beads (and particles) located in the left five lanes would exit via the target exit, while those in the right five lanes would exit from the waste exit. As shown in FIG. 8c, the magnetic force caused the beads to concentrate to the left, with 90.3% located in Lane 1, and 96.2% falling within Lanes 1-5. On the other hand, without the magnetic field, the majority of beads remained in the right lanes, with 96.7% of them in Lanes 6-10 and exiting from the right-side waste exit (FIG. 8c). These results substantiate that the deflection and separation of the magnetic beads from its original streams was indeed caused by the presence of the magnetic field.

Example 5

Characterization of the Microfluidic Device

This study investigated a complete microfluidic device with incubator portion and the separator portion integrated on a single chip (e.g., the device manufactured according to Example 1). With the similar experimental setup as in Example 2, a suspension of premixed target and non-target microparticles into the incubator portion via the sample inlet, and a suspension of magnetic beads via the bead inlet, each at a flow rate of 0.5 µL/min. The particle suspension sample was prepared at two ratios of target to non-target microparticle concentrations (1:1 and 1:10). Deionized water was infused via the buffer inlet into the separator at a flow rate of 4 µL/min. Particle distributions at the end of the separator were investigated to evaluate the ability of the integrated device to capture and isolate target microparticles.

Figure 9:
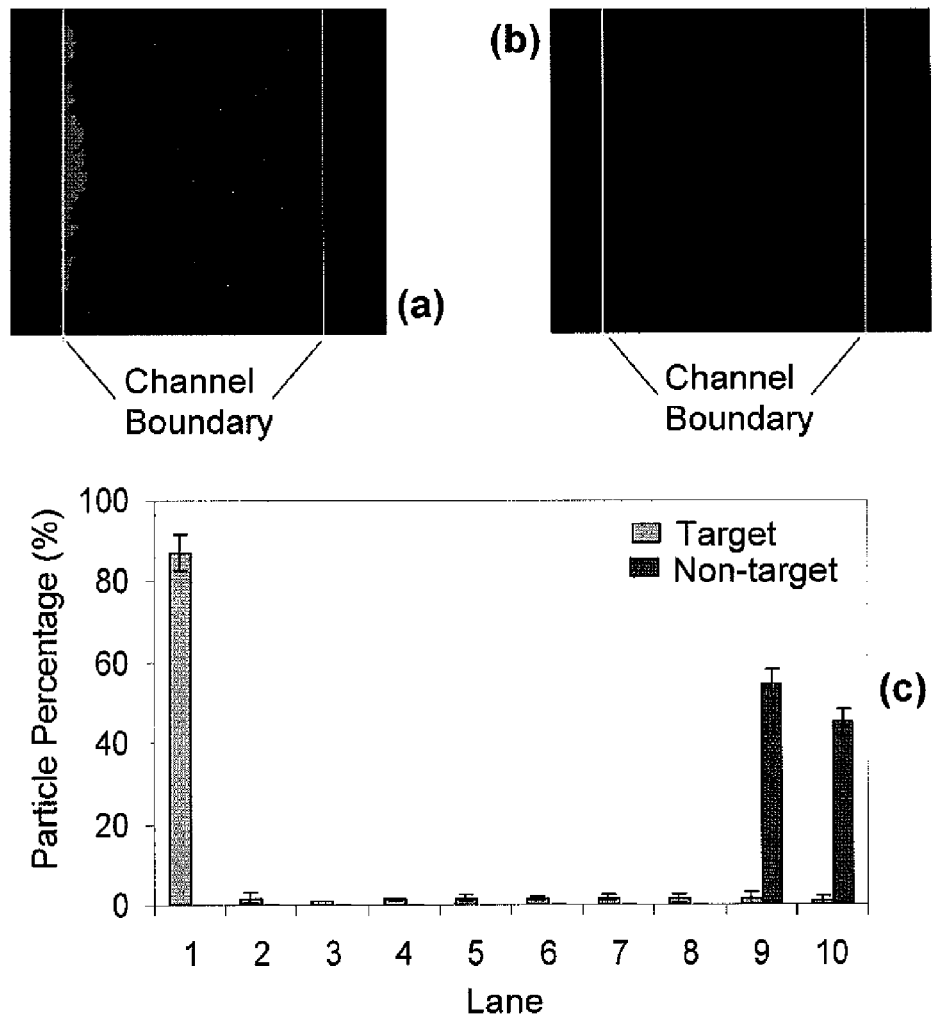
FIG. 9 depicts the distributions of target and non-target microparticle across the channel width at the exit of the separator according to some embodiments of the disclosed subject matter, with a 1:1 ratio of target to non-target microparticle concentrations: (9a) Fluorescent image of target microparticles, and (9b) Fluorescent image of non-target microparticles. (9c) Distributions of the target and non-target microparticles across the channel width.

FIGS. 9a and b presents fluorescence images of target and non-target microparticles, from a sample of 1:1 target to non-target ratio, taken within the separator observation region (FIG. 2) immediately upstream the separator exits. It can be seen that the target and non-target microparticles were clearly separated at the left and right sides of the channel with negligible overlap. Distributions of the particles are extracted from the experimental data and plotted in FIG. 9c beads at the separator exit. The majority of the target microparticles (bound with magnetic beads) were attracted to the left side of the channel, with 87.0% of them contained in Lane 1, while the non-target microparticles remained in Lanes 9 and 10. Overall, 92.7% of target microparticles were retrieved at the target outlet (corresponding to Lanes 1-5), while 99.9% of the non-target microparticles were collected at the waste outlet.

Figure 10:
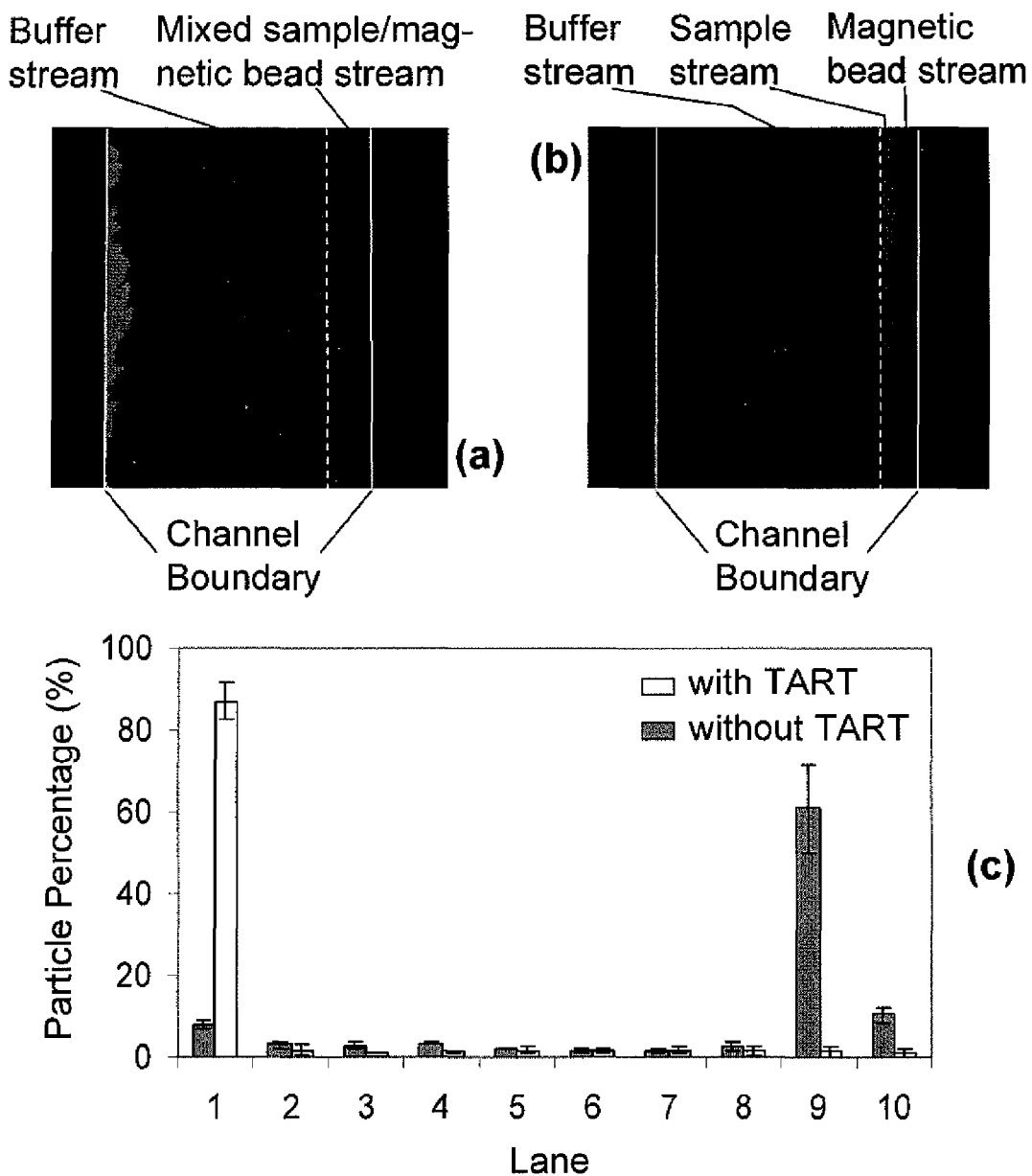
FIG. 10 illustrates a comparison of separation in a microfluidic device according to some embodiments of the disclosed subject matter, with and without applying the magnetic field to the incubator of the device: (10a) Florescent image of target microparticles for incubation under an applied magnetic field applied; (10b) Florescent image of target microparticles for incubation in the absence of a magnetic field; and (10c) Percentage distributions of target microparticles across the channel width at the end of the separator.

The crucial role of the TART scheme in the capture of target microparticles was also investigated with this integrated device. To this end, the distributions of target microparticles at the end of the separator following incubation with and without TART were examined. When TART was enabled, target microparticles were successfully captured by magnetic beads and then deflected by magnetic force to the left of the separator as shown in FIG. 9a, which is duplicated in FIG. 10a for purposes of comparison. In the case of incubation without TART, target microparticles largely remained free from magnetic beads and stayed on the right side of the separator. The dashed line (in white) superimposed on the images indicates the interface between the streams entering the separator from the buffer inlet and incubator exit (FIG. 2). These two streams had become well mixed in the incubator due to agitation by TART-enabled magnetic bead migration (FIG. 10a), but remained well separated by a clearly visible interface when TART was disabled (FIG. 10b). The fluorescent images can be also used to obtain particle percentage distributions across the separator channel width (FIG. 10c): 87% of target microparticles were located in Lane 1 with TART enabled, whereas 71% of target microparticles remained in Lanes 9 and 10 with TART disabled. These results demonstrate that the capture and separation of target microparticles were successful with TART, and failed in the absence of TART.

Figure 11:
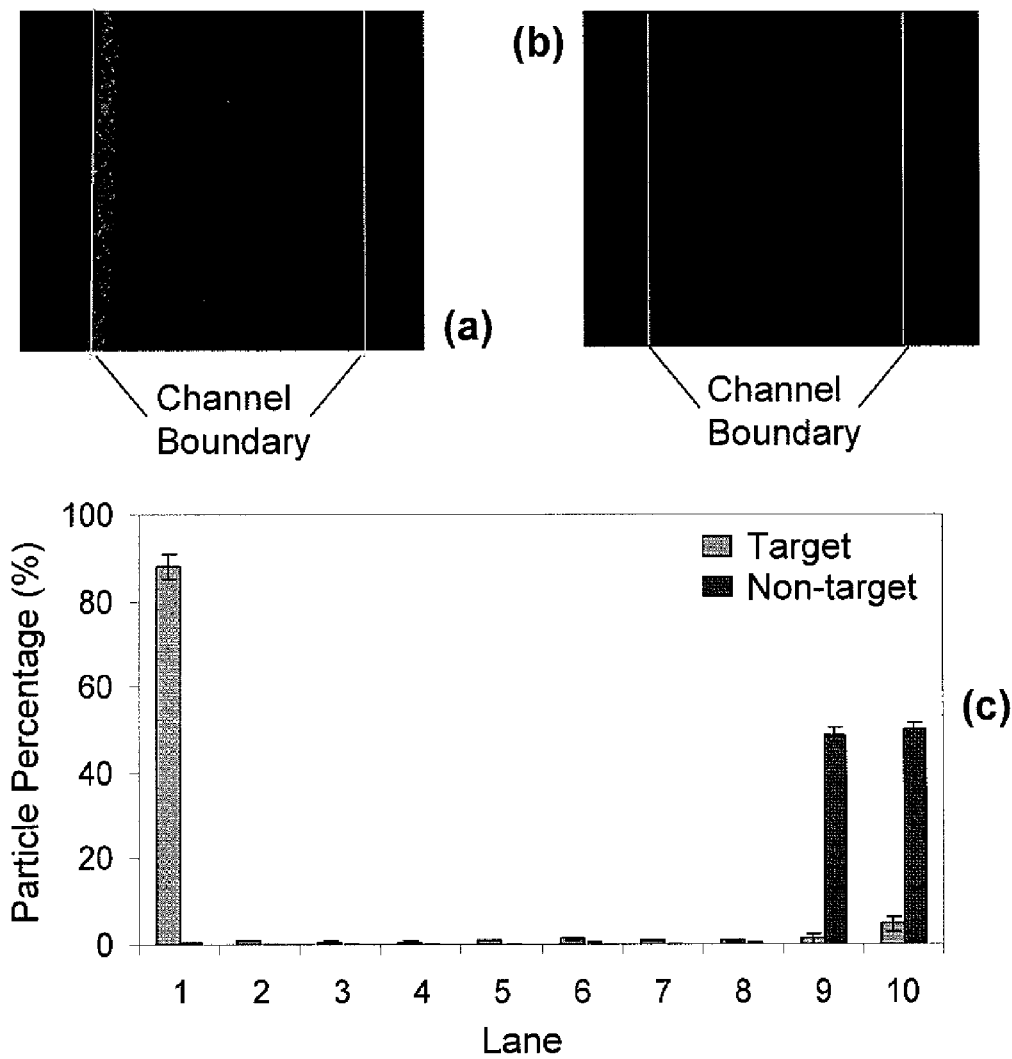
FIG. 11 depicts the distributions of target and non-target microparticles across channel width at the exit of the separator according to some embodiments of the disclosed subject matter, with a 1:10 ratio of target to non-target microparticle concentrations: (11a) Fluorescent image of target microparticles; (11b) Fluorescent image of non-target microparticles; and (11c) Distribution of target and non-target microparticles in transverse lanes across the channel width.

Separation results with TART enabled obtained from another sample with a 1:10 ratio of target to non-target microparticle concentrations were qualitatively the same (FIG. 11a), except that lower fluorescent intensities were obtained due to the lower relative concentration of target microparticles in the sample with respect to non-target microparticles. Specifically, 88.0% of the target microparticles were obtained in Lane 1. Overall, 91.1% and 99.3% of the target and non-target microparticles were respectively collected at their respective outlets.

In general, the target capture and separation efficiency increases with the concentration of magnetic beads, and approaches 100% at sufficiently high bead concentrations. The efficiency observed in the experiment example (92.7% and 91.1% respectively for the 1:1 and 1:10 target vs. non-target ratios) compares favorably with other magnetically controlled particle separation devices incorporating different (e.g., diffusion-based) on-chip incubation schemes. The capture and separation efficiency can be further improved with a higher magnetic bead concentration, which is however associated with an increased tendency of excessive bead retention and channel clogging.

The foregoing merely illustrates the principles of the disclosed subject matter. Various modifications and alterations to the described embodiments will be apparent to those skilled in the art in view of the teachings herein. It will be appreciated that those skilled in the art will be able to devise numerous modifications which, although not explicitly described herein, embody the principles of the disclosed subject matter and are thus within its spirit and scope.

What is claimed is:

1. A device for capturing target microparticles from a fluid comprising the target microparticles, non-target microparticles, and magnetic beads having a stronger affinity with the target microparticles than with the non-target microparticles, comprising:
   a multidirectional microchannel including successive segments connected by turns, each segment having a first side and a second side permitting the fluid to flow therebetween wherein the microchannel comprises:
     a first segment having a first width and located a first distance from the one or more magnets; and
     a second segment having a second width located at a second distance from the one or more magnets, the second distance being greater than the first distance and the second width being greater than the first width; and
   one or more magnets positioned such that each of the one or more magnets is closer to the first side of each of the segments than the second side, wherein the one or more magnets apply a magnetic field to the fluid while the fluid is flowing through at least a portion of the microchannel to thereby repeatedly move the magnetic beads from the first sides to the second sides of the successive segments as the magnetic beads are carried by the fluid flowing through the portion of the microchannel to effect capture of at least a portion of the target microparticles onto the magnetic beads.

2. The device of claim 1, further comprising: a first inlet, coupled to the microchannel, for introducing the target microparticles and non-target microparticles into the microchannel, and a second inlet, coupled to the microchannel, for introducing a suspension including the magnetic beads into the microchannel.

3. The device of claim 1, further comprising a separator portion, fluidically coupled with the microchannel and configured to isolate the target microparticles from the fluid.

4. The device of claim 3, wherein the separator portion further comprises a buffer inlet for introducing a buffer to the fluid so as to isolate the target particles.

5. The device of claim 3, further comprising a target microparticle collection outlet, coupled to the separator portion, for collecting magnetic beads-bound target microparticles.

6. The device of claim 3, wherein the separator portion is formed on the same substrate as the microchannel.

7. The device of claim 1, wherein the one or more magnets comprises a single magnet.

8. The device of claim 1, wherein the one or more magnets comprise a permanent magnet.

* * * * *